United States Patent [19]
Butler et al.

[11] Patent Number: 5,744,483
[45] Date of Patent: Apr. 28, 1998

[54] NEUROPROTECTIVE COMPOUNDS

[75] Inventors: Todd W. Butler, Salem; Bertrand L. Chenard, Waterford, both of Conn.

[73] Assignee: Pfizer Inc., New York, N.Y.

[21] Appl. No.: 687,542

[22] PCT Filed: Nov. 21, 1994

[86] PCT No.: PCT/IB94/00365

§ 371 Date: Oct. 24, 1996

§ 102(e) Date: Oct. 24, 1996

[87] PCT Pub. No.: WO95/20587

PCT Pub. Date: Aug. 3, 1995

[51] Int. Cl.$^6$ .................. A61K 31/445; C07D 405/04
[52] U.S. Cl. ........................... 514/320; 546/196
[58] Field of Search ..................... 514/320; 546/196

[56] References Cited

U.S. PATENT DOCUMENTS

| | | | |
|---|---|---|---|
| 3,294,804 | 12/1966 | Carobateas | 260/294.3 |
| 3,509,164 | 4/1970 | Carron et al. | 260/294.7 |
| 4,016,281 | 4/1977 | Jonas et al. | 424/267 |
| 4,048,317 | 9/1977 | Watts | 424/264 |
| 4,082,755 | 4/1978 | van Wijngaarden et al. | 260/293.6 |
| 4,304,915 | 12/1981 | Berthold | 546/201 |
| 4,358,456 | 11/1982 | Ward | 424/267 |
| 4,393,069 | 7/1983 | Langbein et al. | 424/265 |
| 4,446,113 | 5/1984 | Evans et al. | 422/267 |
| 4,610,992 | 9/1986 | Evans et al. | 514/320 |
| 4,640,422 | 2/1987 | Willcocks | 514/422 |
| 4,711,899 | 12/1987 | Gaudilliere et al. | 514/330 |
| 4,902,695 | 2/1990 | Ornstein | 514/307 |
| 4,957,928 | 9/1990 | Froestl | 514/318 |
| 4,968,678 | 11/1990 | Ornstein | 514/222.2 |
| 4,968,878 | 11/1990 | Pong | 250/221 |
| 5,034,401 | 7/1991 | Frost | 514/323 |
| 5,112,855 | 5/1992 | Froestl | 514/456 |
| 5,192,751 | 3/1993 | Thor | 514/82 |
| 5,356,905 | 10/1994 | Butler | 514/320 |

FOREIGN PATENT DOCUMENTS

WO9014088 11/1990 WIPO.
WO9112005 8/1991 WIPO.

OTHER PUBLICATIONS

Chem. Abst., v. 89, p. 644, No. 43498y, 1978.
Chem. Abst., v. 89, p. 615, No. 146932q, 1978.
J. W. Olney, Annu. Rev. Pharmacol. Toxicol. 1990, 30:47–71.
J. P. Bonte et al., Eur. J. Med. Chem., 25, 1990, pp. 361–368.
D. D. Schoepp et al., J. Neural. Transm. [GenSect], 85, pp. 131–143, 1991.
C. Carron et al., Arzneim.–Forsch. (Drug Res.) 12, pp. 1992–1998, 1971.
K. A. Trujillo et al., Science, v. 251, pp. 85–87, 1991.
N. L. Harrison et al., J. Pharmac., 84, pp. 381–391, 1985.
D. E. Murphy et al., Br. J. Pharmacol., 95, pp. 932–938, 1988.
J. J. Hansen et al., Med. Res. Rev., 10(1), pp. 55–94, 1990.
H. Wachtel et al., TIPS, v. 11, pp. 219–220, 1990.
J. Kornhuber, TIPS, v. 11, p. 357, 1990.
J. Lehmann, Drugs of the Future, 14(11), pp. 1059–1071, 1989.
W. J. Schmidt et al., Pharmac. Biochem. & Behavior, v. 32, pp. 624–623, 1989.
I. A. Shalaby et al., J. Pharm. Exp. Therap., 260(2), pp. 925–931, 1992.
Chem. Abst. v. 89, p. 644, No. 43498y, 1978.
Chem. Abst. v. 89, p. 615, No. 146938w, 1978.

*Primary Examiner*—C. Warren Ivy
*Assistant Examiner*—Charanjit S. Aulakh
*Attorney, Agent, or Firm*—Peter C. Richardson; Paul H. Ginsburg; Bryan C. Zielinski

[57] ABSTRACT

3R*4S*3-[4-(4-fluorophenyl)-4-hydroxy-piperidin-1-yl]-chroman-4,7-diol, its enantiomers and pharmaceutically acceptable salts are effective oral agents for treating diseases and conditions susceptible to treatment by NMDA blocking drugs.

17 Claims, No Drawings

NEUROPROTECTIVE COMPOUNDS

BACKGROUND OF THE INVENTION

This application is 371 of PCT/IB94/00365 which is now published as WO 95/20587 on Aug. 3, 1995.

The present invention is directed to neuroprotective (antiischemic and excitatory amino acid receptor blocking) 3R* 4S* 3-[4-(4-fluorophenyl)-4-hydroxy-piperidin-1-yl]-chroman-4,7-diol; enantiomers thereof; pharmaceutically acceptable salts thereof; and a method of using these compounds in the treatment of head trauma, stroke or CNS degenerative diseases such as Alzheimer's disease, Huntington's disease, Parkinson's disease and other conditions alleviated by blocking the N-methyl-D-aspartic acid (NMDA) receptor.

The excitatory amino acids are an important group of neurotransmitters that mediate excitatory neurotransmission in the central nervous system. Glutamic acid and aspartic acid are two endogenous ligands that activate excitatory amino acid (EAA) receptors. There are two types of EAA receptors, ionotropic and metabotropic, which differ in their mode of signal transduction. There are at least three distinct ionotropic EAA receptors characterized by the selective agonist that activate each type: the NMDA, (N-methyl-D-aspartic acid), the AMPA (2-amino-3-(5-methyl-3-hydroxyisoxazol4-yl)propanoic acid), and the kainic acid receptors. The ionotropic EAA receptors are linked to ion channels that are permeable to sodium and, in the case of NMDA receptors, calcium. Metabotropic receptors, linked to phosphoinositide-hydrolysis by a membrane associated G-protein, are activated by quisqualic acid, ibotenic acid, and (1S,3R)-1-aminocyclopentane 1,3-dicarboxylic acid.

The NMDA receptor is a macromolecular complex consisting of a number of distinct binding sites that gate an ion channel permeable to sodium and calcium ions. Hansen and Krogsgaard-Larsen, *Med. Res. Rev.*, 10, 55–94 (1990). There are binding sites for glutamic acid, glycine, and polyamines, and a site inside the ion channel where compounds such as phencyclidine (PCP) exert their antagonist effects.

Competitive NMDA antagonists are compounds which block the NMDA receptor by interacting with the glutamate binding site. The ability of a particular compound to competitively bind to the NMDA glutamate receptor may be determined using a radioligand binding assay. See Murphy et al. *British J. Pharmacol.* 95, 932–938 (1988). The antagonists may be distinguished from the agonists using a rat cortical wedge assay. See Harrison and Simmonds, *British J. Pharmacol.*, 84, 381–391 (1984). Examples of competitive NMDA antagonists include D-2 amino 5-phosphonopentanoic acid (D-AP5), and D-2-amino-7-phosphonoheptanoic acid, Schoepp et al., *J. Neur. Transm.*, 85, 131–143 (1991).

Antagonists of neurotransmission at NMDA receptors are useful therapeutic agents for the treatment of neurological disorders. U.S. Pat. No. 4,902,695 is directed to a series of competitive NMDA antagonists useful for the treatment of neurological disorders, including epilepsy, stroke, anxiety, cerebral ischemia, muscular spasms, and neurodegenerative disorders such as Alzheimer's disease and Huntington's disease. U.S. Pat. No. 4,968,878 is directed to a second series of competitive NMDA receptor antagonists useful for the treatment of similar neurological disorders and neurodegenerative disorders. U.S. Pat. No. 5,192,751 provides a method of treating urinary incontinence in a mammal which comprises administering an effective amount of a competitive NMDA antagonist.

NMDA antagonists are also useful therapeutic agents with anticonvulsant, anxiolytic, muscle relaxant, and antipsychotic activity, J. Lehmann, *The NMDA Receptor, Drugs of the Future* 14, No. 11, p. 1059 (1989). NMDA antagonists have also been reported to be effective for treating migraine (*Can. J. Neurol. Sci.* 19 (4), p. 487, 1992); drug addiction (*Science*, 251, p. 85, 1991); and neuro-psychiatric disorders related to AIDS (*PIPS* 11, p.1, 1990).

Co-pending, commonly owned U.S. patent application Ser. No. 07/916,130 (European Patent Application 0 441, 506 A3, published Jan. 24, 1991) discloses neuroprotective compounds of the formula:

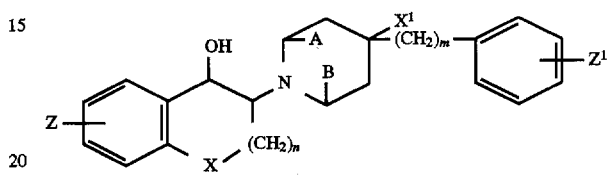

wherein A and B are taken together and are —$CH_2CH_2$— or A and B are taken separately and are each H;

X is $CH_2$ or O;

$X^1$ is H or OH;

Z is H, F, Cl, Br or OH;

$Z^1$ is H, F, Cl, Br or ($C_1$–$C_3$) alkyl;

n is 0 or 1; and m is 0 or an integer from 1 to 6;

and to the pharmaceutically acceptable salts thereof.

Ifenprodil is a racemic, so-called dl-erythro compound having the relative stereochemical formula

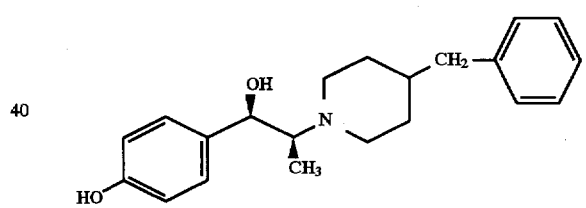

which is marketed as a hypotensive agent, a utility shared by a number of close analogs; Carron et al., U.S. Pat. No. 3,509,164; Carron et al., Drug Res., v. 21, pp. 1992–1999 (1971). More recently, ifenprodil has been shown to possess antiischemic and excitatory amino acid receptor blocking activity; Gotti et al., *J. Pharm. Exp. Therap.*, v. 247, pp. 1211–21 (1988); Carter et al., loc. cit., pp. 1222–32 (1988). See also published European patent application 322,361 and French Patent 2546166. A goal, met by the present invention, has been to find compounds possessing such neuroprotective effect in good measure, while at the same time having lowered or no significant hypotensive effect.

Certain structurally related 1-phenyl-3-(4-aryl-4-acyloxypiperidino)-1-propanols have also been reported to be useful as analgesics, U.S. Pat. No. 3,294,804; and 1-[4-(amino- and hydroxy-alkyl)phenyl]-2-(4-hydroxy-4-tolylpiperazino)-1-alkanols and alkanones have been reported to possess analgesic, antihypertensive, psychotropic or antiinflammatory activity, Japanese Kokai 53-02,474 (CA 89:43498y; Derwent Abs. 14858A) and 53-59,675 (CA 89:146938w; Derwent Abs. 48671 A).

SUMMARY OF THE INVENTION

This invention is directed toward neuroprotective chromanol compounds of formula (I)

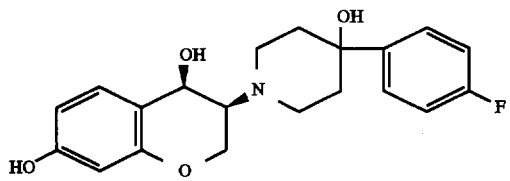

(I)

which possess exceptional oral activity. Optical isomers as well as pharmaceutically acceptable salts of compound (I) are also the subject of this invention.

The present invention is further directed to pharmaceutical compositions comprising a compound of the formula (I) and a pharmaceutically acceptable carrier.

In another aspect, this invention provides a method of blocking NMDA receptor sites in a mammal in need of said blocking compirsing administering to said mammal an effective amount of a compound of formula (I).

In yet another aspect this invention provides a method of treatment of a disease or condition in a mammal, said disease or condition being susceptible to treatment by blocking of NMDA receptor sites comprising administering to said mammal with an effective amount of compound of formula (I).

Diseases or conditions susceptible to treatment by a compound of formula (I) include head trauma, spinal cord trauma, stroke and multiinfarct dementia.

Other diseases or conditions susceptable to treatment by a compound of formula (I) include Alzheimer's disease, Huntington's disease, Parkinson's disease, epilepsy, and amytropic lateral sclerosis.

Additional diseases or conditions susceptible to treatment by a compound of formula (I) include pain, AIDS dementia, psychotic conditions, drug addiction, migraine, hypoglycemia and anxiolytic conditions.

Yet another disease or condition susceptible to treatment by compounds of formula (I) is urinary incontinence.

Yet another disease or condition susceptible to treatment by a compound of formula (I) is an ischemic event arising from CNS surgery, open heart surgery or any procedure during which the function of the cardiovascular system is comprised.

DETAILED DESCRIPTION OF THE INVENTION

The neuroprotective chromanols of formula (I) are readily prepared as described in U.S. Ser. No. 07/916,130 which is hereby incorporated by reference.

Compounds of the present invention are conveniently prepared by reacting a suitably protected 7-hydroxy chromanone, e.g. 7-benzyloxychromanone, with bromine in a reaction inert solvent to produce 7-benzyloxy-3,3-dibromochromanone.

The dibromo compound is then reacted with two molar equivalents 4-(4-fluorophenyl)-4-hydroxypiperidine to produce 7-benzyloxy-3-[4-(4-fluorophenyl)-4-hydroxy-piperidin-1-yl-]-chromenone. The reaction is generally carried out in the presence of a base, usually a tertiary amine in a reaction inert solvent such as ethanol or acetonitrile. If desired, the reaction may be catalyzed with up to one molar equivalent of an iodide salt. Temperature is not critical, but should not be so high as to lead to undue decomposition. A temperature in the range of ambient to 100° C. is generally satisfactory.

The chromenone obtained as described above is reduced to the chromanol using conventional hydride reducing agents, e.g. $NaBH_4$ in a reaction inert solvent such as methanol or ethanol generally at ambient or somewhat higher temperature.

In a final step, the protecting group, e.g. benzyloxy is removed by conventional methods e.g. catalytic hydrogenation to produce compound (I).

If desired, compound (I) may be converted to a pharmaceutically acceptable salt.

The above reference to "pharmaceutically acceptable salts" refers to conventional acid addition salts and cations salts. Thus the compounds of the formula (I) contain an amine group which is basic, and so are capable of forming such salts. Said salts include, but are not limited to, those with HCl, HBr, $HNO_3$, $H_2SO_4$, $H_3PO_4$, $CH_3SO_3H$, p-$CH_3C_6H_4SO_3H$, $CH_3CO_2H$, gluconic acid, tartaric acid, maleic acid and succinic acid. They are generally prepared by conventional methods, e.g. by combining a compound- of the formula (I) with at least one molar equivalent of the acid in a suitable solvent. The compounds of formula (I) contain a phenolic hydroxy group and are also capable of forming cationic salts (e.g., Na, K and the like); the phrase "pharmaceutically acceptable salts" is also intended to encompass such salts. These salts, too, are prepared by conventional methods, e.g., by combining a phenolic compound of the formula (I) which one molar equivalent of NaOH or KOH in a suitable solvent.

The compounds of the formula (I) contain two asymmetric carbons-corresponding to two racemates and four optically active compounds. One of these racemates is the above noted cis-isomer, and the other the trans-isomer. In the present invention the cis isomer predominates and is the preferred form. Each of these racemates is capable of resolution into a pair of enantiomers via diastereomeric acid addition salts with an optically active acid. Alternatively, the racemic alcohol is converted to corresponding diastereomeric esters or urethanes formed with an optically active acid or isocyanate. Such covalently bonded derivatives are subjectable to a variety of separation methods (e.g., chromatography, recrystallization, etc.). Such diastereomeric esters are formed from the alcohol and the optically active acid by standard methods, generally those involving activation of the acid, e.g., as the acid chloride, as a mixed anhydride with an alkyl chloroformate, or with a dehydrative coupling agent such as dicyclohexylcarbodiimide. Once the resulting diastereomeric esters are separated, e.g., by chromatographic methods, they are hydrolyzed by conventional methods, e.g., aqueous acid or aqueous base, to obtain the enantiomeric, optionally active alcohol compounds of the formula (I). Preferred compounds of the present invention are (±) cis and (+) cis isomers. A particularly preferred compound is (+) (3R, 4S)-3-[4-(4-Fluorophenyl)-4-hydroxy-piperidin-1-yl]-chroman-4,7-diol tartrate ethanolate hydrate.

The starting materials and reagents required for the synthesis of the compounds of the present invention are readily available, either commercially, according to literature methods, or by methods exemplified in Preparations below.

The present compounds of the above formula (I) possess selective neuroprotective activity, based upon their antiischemic activity and ability to block excitatory aminoacid receptors, while at the same time having lowered or no significant hypotensive activity. The antiischemic activity of the present compounds is determined according to one or more of the methods which have been detailed previously by Gotti et al. and Carter et al. cited above, or by similar methods. The ability of the compounds of the present invention to block excitatory amino acid receptors may be demonstrated by their ability to block N-methyl-D-aspartic acid-induced (NMDA) elevations of cGMP in neonatal rat cerebellums according to the following procedure. Cerebellums from ten 8–14 day old Wistar rats are quickly excised and placed in 4° C. Krebs/bicarbonate buffer, pH 7.4 and then chopped in 0.5 mm×0.5 mm sections using a McIlvain tissue chopper (The Nickle Laboratory Engineering Col, Gomshall, Surrey, England). The resulting pieces of cerebellum are transferred to 100 ml of Krebs/bicarbonate buffer at 37° C. which is continuously equilibrated with 95:5 $O_2/CO_2$. The pieces of cerebellum are incubated in such a manner for ninety minutes with three changes of the buffer. The buffer then is decanted, the tissue centrifuged (1 min., 3200 r.p.m.) and the tissue resuspended in 20 mL. of the Krebs/bicarbonate buffer. Then, 250 µl aliquots (approximately 2 mg) are removed and placed in 1.5 ml microfuge tubes. To those tubes are added 10 µl of the compound under study from a stock solution followed, after a 10 minute incubation period, by 10 µl of 2.5 mM solution of NMDA to start the reaction. The final NMDA concentration is 100 µM. Controls do not have NMDA added. The tubes are incubated for one minute at 37° C. in a shaking water bath and then 750 µl of a 50 mM Tris-Cl, 5 mM EDTA solution is added to stop the reaction. The tubes are place immediately in a boiling water bath for five minutes. The contents of each tube then are sonicated for 15 seconds using a probe sonicator set at power level three. Ten microliters are removed and the protein determined by the method of Lowry, Anal. Biochem. 100: 201–220 (1979). The tubes are then centrifuged (5 min., 10,000 ×g), 100 µl of the supernatant is removed and the level of cyclic GMP (cGMP) is assayed using a New England Nuclear (Boston, Mass.) cGMP RIA assay according to the method of the supplier. The data is reported as pmole cGMP generated per mg. protein. Undesired hypotensive activity is also determined by known methods, for example, according to the methods of Carron et al., also cited above.

An alternative and preferred procedure for the evaluation of neuroprotective activity is that of Ismail A. Shalaby, et al., *J. Pharm. and Experimental Therapeutics*, 260, 925 (1992) which is hereby incorporated by reference and described below.

Cell culture. Seventeen day fetal rat (CD, Charles River Breeding Laboratories, Inc., Wilmington, Mass.) hippocampal cells were cultured on PRIMARIA culture plates (Falcon Co., Lincoln Park, N.J.) for 2 to 3 weeks in serum containing culture medium (minimum essential medium with nonessential amino acids, containing 2 mM glutamine, 21 mM glucose, penicillin/streptomycin (5000 U each), 10% fetal bovine serum (days 1–7) and 10% horse serum (days 1–21) (Choi et al., 1987). Cells were either plated on 96-well microtiter plates at a density of 80,000 cells per well or on 24-well culture plates at a density of 250,000 cells per well. Cultures were grown at 37° C. in a humidified $CO_2$ tissue culture incubator containing 5% $CO_2$-95% air. Proliferation of nonneuronal cells was controlled by adding 20 µM uridine and 20 µM 5-fluoro-2-deoxyuridine (Sigma Chemical Co., St. Louis, Mo.) from days 6 to 8 of culture (Martin et al., 1990). Culture media was exchanged every 2 to 3 days with fresh stock.

Glutamate toxicity. The cultures were assessed for glutamate toxicity 2 to 3 weeks from initial plating. Culture media was removed and cultures rinsed twice with a CSS (Choi et al., 1987) (in millimolar:): NaCl, 120; KCl, 5.4; $MgCl_2$, 0.8; Ca $Cl_2$, 1.8; glucose, 15; and 4-(2-hydroxyethyl)-1-piperazineethanesulfonic acid, 25 mM (pH 7.4). Cultures were then exposed for 15 min (37° C.) to various concentrations of glutamate. After this incubation, cultures were rinsed 3 times with glutamate-free CSS and twice with fresh culture medium without serum. The cultures were then incubated for 20 to 24 hr in serum-free culture medium. Drugs were added 2 min before and during the 15-min exposure to glutamate. In some experiments, drugs were added at different times after the glutamate exposure and for the following 20 to 24 hr.

Cell viability was routinely assessed 20 to 24 hr after the excitotoxin exposure by measuring the activity of the cytosolic enzyme LDH (Koh and Choi, 1987; Wroblewski and LaDue, 1955). LDH activity was determined from the culture medium of each of the 96 wells of the microtiter plates. A 50-µl sample of the media was added to an equal volume of sodium-phosphate buffer (0.1M, pH 7.4) containing 1.32 mM sodium pyruvate and 2.9 mM NADH. The 340 nm absorbance of the total reaction mixture for each of the 96 wells was monitored every 5 sec for 2 min by an automated spectrophotometric microtiter plate reader (Molecular Devices; Menlo Park, Calif.). The rate of absorbance was automatically calculated using an IBM SOFTmax program (version 1.01; Molecular Devices) and was used as the index of LDH activity.

Morphological assessment of neuronal viability was determined using phase contrast microscopy. The 96-well culture plates did not permit good phase-contrast imagery, so cells cultured on 24-well plates were used for this purpose. Quantitatively, both culture platings were equally sensitive to glutamate toxicity, and displayed 2- to 3-fold increases in LDH activity 24 hr after exposure to 0.1 to 1.0 mM glutamate.

Reagents. DTG was purchased from Aldrich Chemical Company (Milwaukee, Wis.), and haloperidol from Research Biochemicals Inc. (Natick, Mass.). Spermine was purchased from Sigma Chemical Co. (St. Louis, Mo.). Horse and fetal bovine serum were purchased from Hyclone (Logan, Utah). Culture medium, glutamine and penicillin/streptomycin were purchased from Gibco Co. (Grand Island, N.Y.).

Data analysis. Neurotoxicity was quantified by measuring the activity of LDH present in the culture medium 20 to 24 hr after glutamate exposure. Our initial experiments confirmed published reports indicating that the increased LDH activity in the culture media correlates with destruction and degeneration of neurons (Koh and Choi, 1987). Because actual levels of LDH varied from different cultures, data were routinely expressed relative to buffer-treated sister wells of the same culture plate. To obtain an index of LDH activity from glutamate and drug-treated cultures, the LDH values from control cultures were subtracted from that of the treatment groups. Data for drug treatments was expressed as a percentage of the increase in LDH induced by 1 mM glutamate (or NMDA) for each experiment. Concentrations of NMDA antagonists required to reverse 50% of the LDH increase induced by excitotoxins ($IC_{50}$) were calculated using log-probit analysis from the pooled results of three independent experiments. Different treatment groups were compared using a two-tailed t test.

Such selective neuroprotective antiischemic and excitatory amino acid blocking activities reflect the valuable utility of the present compounds in the treatment of degenerative CNS (central nervous system) disorders such as stroke; and Alzheimer's disease, Parkinson's disease and Huntington's disease; without significant potential for concurrent undue drop in blood pressure. In the systemic treatment of such diseases with a neuroprotective amount of compounds of the formula (I), the dosage is typically from about 0.02 to 10 mg/kg/day (1–500 mg/day in a typical human weighing 50 kg) in single or divided doses, regardless of the route of administration. Of course, depending upon the exact compound and the exact nature of the individual illness, doses outside this range may be prescribed by the attending physician. The oral route of administration is generally preferred. However, if the patient is unable to swallow, or oral absorption is otherwise impaired, the preferred route of administration will be parenteral (i.m., i.v.) or topical.

The compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; and for topical administration, in the form of solutions, lotions, ointments, salves and the like.

Oral administration is preferred and oral bioavailability is an important parameter in selecting compounds which are especially useful as NMDA antagonists. Oral bioavailability may be evaluated by the method devised by Schmidt and Bubser (Pharmacol. Biochem. Behavior, 1989, 32, 621) which measures the ability of an oral dose of the test compound to reverse catalepsy induced by haloperidol.

Male Sprague-Dawley rats (Interfauna, Tutlingen, F.R.G.) received intraperitoneal (IP) injections of 0.5 mg/kg haloperidol (injectable solution from ampoules, Jansen, Neuss, (F.R.G.) in order to induce a moderate degree of catalepsy. Simultaneously, either a compound of formula (I) in an inert carrier or the inert carrier were administered orally. The solution for oral administration was prepared by dissolving the compound in 0.3% aqueous tartaric acid. Solid tartaric acid acid was added to bring the pH to 3.5. Thirty minutes after treatment the degree of catalepsy was measured in each rat. Three established tests may be carried out in the following order of succession:

1) Placing both forelegs on a horizontal bar 9 cm above the surface.

2) Placing one foreleg on a podium (3 cm high).

3) Hanging on a vertical wire grid.

The time span from placement of the paws until the first movement of one of these paws (descent latency) was measured (at the most for 180 sec).

Differences between groups were analyzed using the two-tailed Mann-Whitney U-test. A p-value <0.05 was considered to indicate a significant difference between groups.

We unexpectedly found that the compound of formula (I) is significantly more effective in an oral dose than are other compounds described in U.S. Ser. No. 07/916,130.

The present invention is illustrated by the following examples, but is not limited to the details thereof.

PREPARATIONS AND EXAMPLES

All non-aqueous reactions were run under nitrogen for convenience and generally to maximize yields. All solvents/ diluents were dried according to standard published procedures or purchased in a predried form. All reactions were stirred either magnetically or mechanically. NMR spectra are recorded at 250 or 300 MHz and are reported in ppm. The NMR solvent was $CDCl_3$ unless otherwise specified. IR spectra are reported in $cm^{-1}$, generally specifying only strong signals. The following abbreviations are used: DMF for dimethylformamide, THF for tetrahydrofuran, HRMS for high resolution mass spectrum.

PREPARATION 1

7-Benzyloxychromanone

A mixture of 7-hydroxychromanone (10.0 g, 61 mmol), benzyl bromide (7.6 mL, 64 mmol), and potassium carbonate (16.5 g, 120 mmol) in acetone (250 mL) was gently refluxed 24 h. The mixture was cooled and filtered through celite. The filtrate 20 was concentrated and the residue was taken up in ethyl acetate. The organic solution was washed with water and brine, dried over calcium sulfate, and concentrated to a tan solid. Recrystallization from ethanol gave 12.63 g (81%) of 7-benzyloxychromanone as tan crystal which had mp 99°–102° C.; NMR δ7.85 (d, J=9 Hz, 1H), 7.44–7.32 (m,5H), 6.66 (dd, J=2.4, 9Hz, 1H), 6.49 (d, J=2.4 Hz, 1H), 5.09 (s,2H), 4.52 (t, J=6.5 Hz, 2H), 2.76 (t, J=6.5 Hz, 2H).

Analysis calculated for $C_{16}H_{14}O_3$: C, 75.58; H, 5.55 Found: C, 75.44; H, 5.58.

PREPARATION 2

7-Benzyloxy-3,3-dibromochromanone

To a slurry of 7-benzyloxychromanone (12.63 g, 49.7 mmol) in carbon tetrachloride (200 mL) and ethyl acetate (100 mL) was added a solution of bromine (5.38 mL, 104.4 mmol) in carbon tetrachloride (100 mL) over 20 min. The clear red solution was stirred 10 min longer, then hydrogen bromide was driven from the reaction with a nitrogen stream (15 min). The organic solution was washed with aqueous sodium bisulfite, aqueous sodium bicarbonate and brine; then R was dried over calcium sulfate and concentrated to an oil which slowly solidified. Recrystallization from ethanol gave 15.73 g (76%) of 7-benzyloxy-3,3-dibromochromanone as pink crystals which had mp 89°–90° C.; NMR δ7.96 (d, J=9 Hz, 1H), 7.43–7.36 (m, 5H), 6.79 (dd, J=2.4, 9 Hz, 1H), 6.57 (d, J=2.4 Hz, 1H), 5.12 (s, 2H), 4.71 (s, 2H).

Analysis calculated for $C_{16}H_{12}Br_2O_3$: C, 46.64; H, 2.94. Found: C, 46.62; H, 2.96.

Example 1

3R*4S* 3-[4-(4-fluorophenyl)-4-hydroxy-piperidin-1 -yl]-chroman-4,7-diol

A mixture of 7-benzyloxy-3,3-dibromochromanone (54.7 g, 133 mmol), 4-(4-fluorophenyl)-4-hydroxypiperidine (52.0 g, 266 mmol), and triethylamine (38 mL, 270 mmol) in acetonitrile (2.5 L) was stirred 16 h at ambient temperature. A yellow precipitate formed and was collected, washed well with water and ether, and air dried. The yield of 7-benzyloxy-3-[4-(4-fluorophenyl)-4-hydroxy-piperidine-1-yl]-chromenone was 55.4 g (93%) which was suitable for use without further purification. A sample recrystallized from ethanol/tetrahydrofuran had mp 220°–221° C.; NMR $DMSO_{d6}$ δ7.99 (d, J=9 Hz, 2H), 7.56–7.40 (m, 8 H), 7.18–7.08 (m, 4H), 5.25 (s, 2H), 5.06 (s, 1H), 3.60 (br s, 1H), 3.55–3.35 (m, 1H, partially obscurred by water from the NMR solvent), 3.10–2.95 (m, 2H), 2.15–2.00 (m, 2H), 1.71 (br t, J=13.7 Hz, 2H).

Analysis calculated for $C_{27}H_{24}FNO_4$: C, 72.80; H, 5.43; N, 3.14. Found: C, 72.83; H, 5.82; N, 2.82.

To a slurry of 7-benzyloxy-3-[4-(4-fluorophenyl)-4-hydroxy-piperidine-1-yl]-chromenone (8.24 g, 18.5 mmol) in ethanol (400 mL) and tetrahydrofuran (600 mL) was added sodium borohydride (7.0 g, 185 mmol). The mixture was stirred overnight. Additional sodium borohydride ((7.0 g) was added and the reaction was stirred 3 days. Water was added and the solvent was removed at reduced pressure at 45° C. The solids which formed were collected and washed well with water and then ether. The solid was further dried in vacuo overnight to give 5.01 g, 60% of 3R*4S* 7-benzyloxy-3-[4-(4-fluorophenyl)-4-hydroxy-piperidin-1-yl]-chroman-4-ol which was suitable for use without further purification. A sample recrystallized from ethyl acetate/chloroform had mp 194°–195° C.; NMR δ7.56–7.30 (m, 8H), 7.06 (long range coupled t, J=8.7 Hz, 2H) 6.63 (dd, J=2.4, 8.5 Hz, 1H), 6.47 (d, J=2.4 Hz, 1H), 5.04 (s, 2H), 4.77 (d, J=4.5 Hz, 1H), 4.36 (dd, J=3.5, 10.4 Hz, 1H), 4.13 (t, J=10.4 Hz, 1H), 3.82 (brs, 1H), 3.11 (br d, J=11.2 Hz, 1H), 2.92–2.71 (m, 4H), 2.21–2.06 (m, 2H), 1.87–1.73 (m, 2H), 1.54 (s, 1H).

Analysis calculated for $C_{27}H_{28}FNO_4$: C, 72.14; H, 6.28; N, 3.12. Found: C, 72.15; H, 6.21; N, 3.12.

A mixture of 3R*4S* 7-benzyloxy-3-[4-(4-fluorophenyl)-4-hydroxy-piperidin-1-yl]-chroman-4-ol (0.80 g, 1.78 mmol), 10% palladium on carbon (0.16 g), methanol (40 mL), and acetic acid (0.8 mL) was hydrogenated for 8 h with a starting pressure of 48.5 psi. The reaction was filtered through celite and the filtrate was concentrated. The residue was stirred vigorously with ether and saturated aqueous sodium bicarbonate for 1 h. The solid product was filtered, washed with water and ether, and dried in vacuo. Recrystallization from ethanol gave 0.35 g (54%) of 3R* 4S* 3-[4-(4-fluorophenyl)-4-hydroxy-piperidin-1-yl]-chroman-4,7-diol as a white solid which had mp 159°–160° C.; NMR $DMSO_{d6}$ δ7.55–7.47 (m, 2H, 7.11 (t, J=9 Hz, 2H, 7.02 (d, J=8.4 Hz, 1H, 6.32 (dd, J=2.3, 8.3 Hz, 1H, 6.15 (d, J=2.3 Hz 1H, 5.10–4.50 (br m with s at 4.63, 3H, 4.23 (dd, J=2.8, 10.3 Hz, 1H, 4.04 (t, J=10.5 Hz, 1H, 2.99 (br d, J=10.8 Hz, 1H, 2.86 (br d, J=10.7 Hz, 1H, 2.73–2.50 (m, 3H, 2.08–1.90 (m, 2H, 1.58 (br d, J=13 Hz, 2H.

Analysis calculated for $C_{20}H_{22}FNO_4 \cdot 0.25\ H_2O$: C, 66.01; H, 6.23; N, 3.85. Found: C, 66.22; H, 6.58; N, 3.46.

Example 2

(+) Enantiomer of 3R 4S 3-[4-(4-fluorophenyl)-4-hydroxy-piperidin-1-yl]-chroman-4,7-diol

A mixture of 3R*4S* 7-benzyloxy-3-[4-(4-fluorophenyl)-4-hydroxy-piperidin-1-yl]-chroman-4-ol(15.22 9, 33.86 mmol), N-tert-butoxycarbonyl-L-proline (14.65 g, 68.06 mmol), 4-dimethylaminopyridine (4.18 g, 34.21 mmol), and 1-ethyl-3-(3-dimethylaminopropyl)-carbodiimide hydrochloride (13.10 g, 68.3 mmol) in methylene chloride was gently refluxed 3 h. The mixture was concentrated at reduced pressure and the residue was partitioned between ethyl acetate and water. The phases were separated and the organic layer was washed with water and brine; then it was dried over calcium sulfate and concentrated to a yellow foam. Isopropyl ether (200 mL) was added and the mixture was briefly heated to the boiling point. This mixture was allowed to return to ambient temperature and stir overnight. The insoluble material was collected and rinsed with isopropyl ether and weighted 9.62 g. This material was recrystallized from ethyl acetate to give 6.43 g (29%) of the (+) enantiomer of the N-tert-butoxycarbonyl-L-proline ester of 3R 4S 7-benzyloxy-3-[4-(4-fluorophenyl)-4-hydroxy-piperidin-1-yl]-chroman-4-ol which had mp 200°–200.5° C.; $[\alpha]_D$=+100.0° c=0.345 (methanol).

Analysis calculated for $C_{37}H_{43}FN_2O_7$: C, 68.71; H, 6.70; N, 4.33. Found: C, 68.36; H, 6.78; N, 4.57. Note that the isopropyl ether filtrate contained the diastereomeric N-tert-butoxycarbonyl-L-proline ester product which could be used to prepare the corresponding (−) title product.

The product of the above reaction (0.262 g, 0.405 mmol) was added to 0° C. slurry of lithium aluminum hydride (0.020 g, 0.527 mmol) in tetrahydrofuran (10 mL). The mixture was allowed to warm to room temperature and stirred 10 min. The reaction was quenched with sodium sulfate decahydrate, dried with sodium sulfate and filtered through celite. The filtrate was concentrated to leave a white solid which was triturated with ether/hexane to yield 0.154 g (85%) of the (+) enantiomer 3R 4S 7-benzyloxy-3-[4-(4-fluorophenyl)-4-hydroxy-piperidin-1-yl]-chroman-4-ol which had mp 178°–178.5° C.; $[\alpha]_D$=+75.4° c=0.305 (methanol); NMR δ7.51–7.30 (m, 8H, 7.06 (t, J=8.7 Hz, 2H, 6.63 (dd, J=2.4, 8.5 Hz, 1 H), 6.47 (d, J=2.3 Hz, 1H, 5.04 (s, 2H, 4.77 (d, J=3 Hz, 1H, 4.36 (dd, J=3.3, 10.5 Hz, 1H, 4.13 (t, J=10.4 Hz, 1H, 3.83 (s, 1H, 3.11 (br d, J=11.1 Hz, 1H, 2.91–2.72 (m, 4H, 2.20–2.05 (m, 2H, 1.86–1.79 (m, 2H, 1.56 (s, 1H; $^{13}C$ NMR δ163.59, 160.05, 154.95, 143.73, 136.84, 131.84, 128.58, 127.96, 127.42, 126.33, 126.22, 115.33, 115.26, 115.05, 108.91, 101.97, 77.22, 70.68, 70.03, 62.46, 61.76, 60.71, 47.05, 45.09, 38.63.

Analysis calculated for $C_{27}H_{28}FNO_4$: C, 72.14; H, 6.28; N, 3.12. Found: C, 71.75; H, 6.45; N, 3.12.

A mixture of the product of the above reaction (1.29 g, 2.87 mmol) and 10% palladium on carbon (0.27 g) in methanol (65 mL) and acetic acid (1.3 mL) was hydrogenated at 50 psi (starting pressure) for 7.25 h. The mixture was filtered through celite and concentrated to an oil. Saturated aqueous sodium bicarbonate (150 mL) and ether (50 mL) were added to the oil and this mixture was vigorously stirred 15 min. The white solid which formed was collected and air dried to give 0.83 g (81%) of the (+) enantiomer of 3R 4S 3-[4(4-fluorophenyl)-4-hydroxy-piperidin-1-yl]-chroman-4,7-diol which had mp 165°–166° C.; $[\alpha]_D$=+85.60° c=0.430 (methanol); NMR $DMSO_{d6}$ δ9.38 (br s, 1H, 7.54–7.50 (m, 2H, 7.12 (t, J=9 Hz, 2H, 7.02 (d, J=8.4 Hz, 1H, 6.32 (dd, J=2.4, 8.3 Hz, 1H, 6.16 (d, J=2.3 Hz, 1H, 4.88 (s, 1H, 4.77 (s, 1H, 4.65 (s, 1H, 4.23 (dd, J=2.5, 10.1 Hz, 1H, 4.05 (t, J=10.6 Hz, 1H, 3.00 (brd, J=10.3 Hz, 1H, 2.87 (brd, J=10.3 Hz, 1H, 2.67 (q, J=11.2 Hz, 2H, 2.54–2.49 (m, 1H, 1.94 (brt, J=11.0 Hz, 2H, 1.59 (br d, J=13 Hz, 2H; $^{13}C$ NMR $DMSO_{d6}$ δ162.41, 159.21, 158.17, 154.58, 146.42, 131.79, 126.88, 126.78, 115.92, 114.52, 114.24, 108.12, 101.83, 69.47, 62.74, 61.95, 61.45, 46.21, 45.82, 38.37, 38.28.

Analysis calculated for $C_{20}H_{22}FNO_4 \cdot 0.25\ H_2O$: C, 66.01; H, 6.23; N, 3.85. Found C, 66.05; H, 6.39; N, 3.84.

Example 3

(−) Enantiomer of 4R 3S 3-[4-(4-fluorophenyl)-4-hydroxy-piperidin-1-yl]-chroman-4,7-diol

The title product was prepared following the procedure of Example 2 using N-tert-butoxycarbonyl-D-proline as the resolving agent. The intermediates and title product so obtained had the following physical characteristics:

(−) Enantiomer of the N-tert-butoxycarbonyl-D-proline ester of 4R 3S 7-benzyloxy-3-[4-(4-fluorophenyl)-4- hydroxy-piperidin-1-yl]-chroman-4-ol: mp 199°–199.5° C.; $[\alpha]_D$=–92.5° c=0.320 (methanol).

Analysis calculated for $C_{37}H_{43}N_2O_7$: C, 68.71; H, 6.70; N, 4.33. Found: C, 68.37; H, 6.84; N, 4.34.

(–) Enantiomer 4R 3S 7-benzyloxy-3-[4-(4-fluorophenyl)-4-hydroxy-piperidin-1-yl]-chroman-4-ol: mp 177°–178° C.; $[\alpha]_D$=–73.0° c=0.330 (methanol).

Analysis calculated for $C_{27}H_{28}FNO_4 \cdot 1.25\ H_2O$: C, 68.70; H, 6.51; N, 2.96. Found: C, 68.76; H, 6.42; N, 3.01.

(–) Enantiomer 4R 3S 3-[4-(4-fluorophenyl)-4hydroxy-piperidin-1-yl]-chroman-4,7-diol: mp 166.5°–167° C.; $[\alpha]_D$=–84.1° c=0.290 (methanol).

Analysis calculated for $C_{20}H_{22}FNO_4 \cdot 0.25\ H_2O$: C, 66.01; H, 6.23; N, 3.85. Found: C, 66.22; H, 6.27; N, 3.96.

Alternatively the soluble L-proline ester from example 2 was hydrolyzed with lithium aluminum hydride under substantially the same conditions as described above to return the starting material for example 2 which is enriched in the (–) enantiomer. This material was treated with N-tert-butoxycarbonyl-D-proline following the procedure of example 2 to produce the title product of this example.

Example 4

(+) (3R,4S)-3-[4-(4-Fluorophenyl)-4-hydroxy-piperidin-1-yl]-chroman-4,7-diol tartrate ethanolate hydrate A mixture of (+) (3R,4S)-3-[4-(4-fluorophenyl)-4-hydroxy-piperidin-1-yl]-chroman-4,7-idol (2.11 g, 5.87 mmol) and tartaric acid (0.885 g, 5.90 mmol, Mallinckrodt, dextrorotatory with levo configuration) in ethanol (20 mL, with warming) was concentrated to an amorphous pale yellow solid which was dried in vacuo overnight to afford 2.995 g (100%) of (+) (3R,4S)-3-[4-(4-fluorophenyl)-4-hydroxy-piperidin-1-yl]-chroman-4,7-diol tartrate ethanolate hydrate which had: mp range 85°–95° C.; $[\alpha]_D$=+55.6°, c=1.140 (methanol); $^1$HNMR $DMSO_{d6}$ δ7.53 (dd, J=5.6, 8.7 Hz, 2H, 7.15 (t, J=8.9 Hz, 2H 7.08 (d, J=8.4 Hz, 1H, 6.81 (brs, 7H, 6.40 (dd, J=2.2, 8.3 Hz, 1H, 6.22 (d, J=2.2 Hz, 1H, 4.85 (s, 1 H), 4.45 (d, J =–8.4 Hz, 1H, 4.21–4.13 (m, 3H, 3.44 (q, J=7.0 Hz, 2H 3.34–3.08 (m, 5H, 2.19 (br q, J=12.9 Hz, 2H, 1.72 (brt, J=11.8 Hz, 2H, 1.06 (t, J=7.0 Hz, 3H $^{13}$C NMR $DMSO_{d6}$ δ174.02, 162.62, 159.41, 158.56, 154.24, 145.10, 131.80, 126.87, 126.77, 114.72, 114.45, 108.80, 101.94, 72.11, 68.55, 61.50, 61.08, 60.35, 56.08, 46.57, 46.09, 36.39, 36.24, 18.57.

Analysis calculated for $C_{20}H_{22}FNO_4 \cdot C_4H_6O_6 C_2H_6OH_2O$; C, 54.45; H, 6.33; N, 2.44. Found: C, 54.51; H, 6.33; N, 2.49.

We claim:

1. A compound 3R*4S*3-[4-(4-fluorophenyl)-4-hydroxy-piperidin-1-yl]-chroman-4,7-diol, its optical isomers and pharmaceutically acceptable salts.

2. The compound of claim 1 which is racemic 3R* 4S* 3-[4-(4-fluorophenyl)-4-hydroxy-piperidin-1-yl]-chroman-4,7-diol.

3. The compound of claim 1 which is (+) 3R 4S 3-[4-(4-fluorophenyl)-4-hydroxy-piperidin-1-yl]-chroman-4,7-diol.

4. The compound of claim 1 which is (–) 4R 3S 3-[4-(4-fluorophenyl)-4-hydroxy-piperidin-1-yl]-chroman-4,7-diol.

5. A pharmaceutical composition comprising a neuroprotective amount of a compound of claim 1 and a pharmaceutically acceptable carrier.

6. A pharmaceutical composition comprising a neuroprotective amount of a compound of claim 2 and a pharmaceutically acceptable carrier.

7. A pharmaceutical composition comprising a neuroprotective amount of a compound of claim 3 and a pharmaceutically acceptable carrier.

8. A pharmaceutical composition of claim 5 which is for oral use.

9. A method of blocking NMDA receptor sites in a mammal in need of said blocking comprising administering to said mammal an effective amount of a compound of claim 1.

10. A method of treatment of a disease or condition in a mammal, said disease or condition being susceptible to treatment by blocking of NMDA receptor sites comprising administering to said mammal with an effective amount of a compound of claim 1.

11. A method of claim 10 wherein said disease or condition is selected from the group consisting of head trauma, spinal cord trauma, stroke and multiinfarct dementia.

12. A method of claim 10 wherein said disease or condition is selected from the group consisting of Alzheimer's disease, Huntington's disease, Parkinson's disease, epilepsy, and amytropic lateral sclerosis.

13. A method of claim 10 wherein said disease or condition is selected from the group consisting of pain, AIDS dementia, psychotic conditions, drug addiction, migraine, hypoglycemia and anxiolytic conditions.

14. A method of claim 10 wherein said disease or condition is urinary incontinence.

15. A method of claim 10 wherein said disease or condition is an ischemic event arising from CNS surgery, open heart surgery or any procedure during which the function of the cardiovascular system is comprised.

16. A method of claim 13 wherein said disease or condition is migraine.

17. The compound of claim 1 which is (+) (3R,4S)-3-[4-(4-fluorophenyl)-4-hydroxy-piperidin-1-yl]-chroman-4,7-diol tartrate ethanolate hydrate.

* * * * *